US009255894B2

United States Patent
VanHoomissen et al.

(10) Patent No.: US 9,255,894 B2
(45) Date of Patent: Feb. 9, 2016

(54) SYSTEM AND METHOD FOR DETECTING CRACKS IN A WAFER

(71) Applicant: KLA-Tencor Corporation, Milpitas, CA (US)

(72) Inventors: William VanHoomissen, San Jose, CA (US); Sean Wheeler, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/073,535

(22) Filed: Nov. 6, 2013

(65) Prior Publication Data

US 2014/0152976 A1    Jun. 5, 2014

Related U.S. Application Data

(60) Provisional application No. 61/724,776, filed on Nov. 9, 2012.

(51) Int. Cl.
*G01N 21/00* (2006.01)
*G01N 21/95* (2006.01)

(52) U.S. Cl.
CPC .................................. *G01N 21/9505* (2013.01)

(58) Field of Classification Search
CPC .......... G01N 21/9501; G01N 21/8806; G01N 21/94; G01N 21/956; G01N 21/88
USPC ....................................................... 356/237.1
See application file for complete search history.

(56) References Cited

U.S. PATENT DOCUMENTS

| | | | |
|---|---|---|---|
| 4,806,776 A * | 2/1989 | Kley | 250/559.24 |
| 5,438,209 A | 8/1995 | Yamamoto et al. | |
| 2003/0053046 A1 | 3/2003 | Ise et al. | |
| 2005/0024632 A1* | 2/2005 | Plemmons et al. | 356/237.1 |
| 2006/0256328 A1* | 11/2006 | Uto et al. | 356/237.2 |
| 2007/0121106 A1* | 5/2007 | Shibata et al. | 356/237.2 |
| 2008/0212084 A1* | 9/2008 | Watkins et al. | 356/237.5 |
| 2010/0014083 A1* | 1/2010 | Ueno et al. | 356/364 |
| 2012/0008132 A1* | 1/2012 | Saito et al. | 356/72 |

FOREIGN PATENT DOCUMENTS

| | | |
|---|---|---|
| JP | 2009288032 | 12/2009 |
| KR | 1020050060644 | 6/2005 |
| KR | 1020070081508 | 8/2007 |

\* cited by examiner

*Primary Examiner* — Tarifur Chowdhury
*Assistant Examiner* — Md Rahman
(74) *Attorney, Agent, or Firm* — Suiter Swantz pc llo

(57) ABSTRACT

A wafer crack detection system includes a rotational wafer stage assembly configured to secure a wafer and selectively rotate the wafer, a light source positioned on a first side of the wafer and configured to direct a light beam through the wafer, a sensor positioned on a second side of the wafer and configured to monitor one or more characteristics of light transmitted through the wafer as the wafer is rotated, and a controller communicatively coupled to the sensor and a portion of the rotational wafer stage assembly, the controller configured to: determine the presence of one or more cracks in the wafer based on the monitored one or more characteristics of light transmitted through the wafer, and, responsive to the determination of the presence of one or more cracks in the wafer, direct the rotational stage assembly to adjust the rotational condition of the wafer.

23 Claims, 8 Drawing Sheets

SYSTEM AND METHOD FOR DETECTING CRACKS IN A WAFER

CROSS-REFERENCE TO RELATED APPLICATIONS

The present application claims priority under 35 U.S.C. §119(e) to U.S. Provisional Application No. 61/724,776 entitled Method of Detecting Cracks in Silicon Wafers filed on Nov. 9, 2012, which is hereby incorporated by reference in the entirety.

FIELD OF THE INVENTION

The present invention generally relates to crack detection in semiconductor wafers, and, in particular, to crack detection in wafers disposed on a rotational wafer stage.

BACKGROUND

As demand for ever-shrinking semiconductor devices continues to increase, so too will the demand for improved semiconductor wafer inspection processes and throughput. One such semiconductor wafer inspection method includes rotation-based wafer inspection techniques. Rotation-based wafer scanning includes the utilization of a rotating wafer stage assembly suitable for rapidly spinning a semiconductor wafer beneath the optics of the inspection tool. Due to the high spinning speeds (upwards of 10,000 RPM), the presence of cracks in the wafer may lead to catastrophic wafer damage, whereby the wafer breaks apart. Wafer damage cause by wafer cracking leads to a reduction in overall inspection throughput. Typically, wafer cracking detection is carried out off-line using optical tools such as an inspection microscope. Off-line optical crack inspection techniques of the prior art are difficult to implement and negatively impact wafer inspection throughput. As such, it is desirable to provide an improved wafer crack detection method and system that acts to cure the defects of the prior art.

SUMMARY OF THE INVENTION

A system for detecting cracks in a wafer is disclosed. In one aspect, the system may include, but is not limited to, a rotational wafer stage assembly configured to secure a wafer and selectively rotate the wafer; a light source positioned on a first side of a surface of the wafer and configured to direct at least a portion of a light beam through the wafer, wherein the light beam is at least partially transmittable through the wafer; a sensor positioned on a second side of the wafer opposite the first side and configured to monitor one or more characteristics of light transmitted through the wafer as the rotational wafer stage assembly rotates the wafer, wherein the rotational wafer stage assembly and the light source are configured to cause the light beam to trace a pattern across the wafer; a controller communicatively coupled to the sensor and a portion of the rotational wafer stage assembly, the controller configured to: determine the presence of one or more cracks in the wafer based on the monitored one or more characteristics of light transmitted through the wafer; and responsive to the determination of the presence of one or more cracks in the wafer, direct the rotational stage assembly to adjust the rotational condition of the wafer.

An inspection tool equipped with crack detection capabilities is disclosed. In one aspect, the inspection tool may include, but is not limited to, a light source configured to illuminate an area of a surface of a wafer disposed on a rotational wafer stage assembly configured to secure a wafer and selectively rotate the wafer; a detector configured to detect light reflected or scattered from the illuminated area of the wafer; a crack detection light source positioned on a first side of a surface of the wafer and configured to direct at least a portion of a light beam through the wafer, wherein the light beam is at least partially transmittable through the wafer; a crack detection sensor positioned on a second side of the wafer opposite the first side and configured to monitor one or more characteristics of light transmitted through the wafer as the rotational wafer stage assembly rotates the wafer, wherein the rotational wafer stage assembly and the light source are configured to cause the light beam to trace a pattern across the wafer; a controller communicatively coupled to the sensor and a portion of the rotational wafer stage assembly, the controller configured to: determine the presence of one or more cracks in the wafer based on the monitored one or more characteristics of light transmitted through the wafer; and responsive to the determination of the presence of one or more cracks in the wafer, direct the rotational stage assembly to adjust the rotational condition of the wafer.

A method for detecting cracks in a wafer is disclosed. In one aspect, the method may include, but is not limited to, generating a light beam at least partially transmittable through the wafer; selectively rotating a wafer disposed on a rotational wafer stage assembly in order to trace the light beam across the surface of the wafer; monitoring one or more characteristics of light transmitted through the wafer; determining the presence of one or more cracks in the wafer based on the monitored one or more characteristics of light transmitted through the wafer; and responsive to the determination of the presence of one or more cracks in the wafer, directing the rotational stage assembly to adjust the rotational condition of the wafer.

A system for monitoring centering of wafer on a rotational wafer stage is disclosed. In one aspect, the system may include, but is not limited to, a rotational wafer stage assembly configured to secure a wafer and selectively rotate the wafer; a light source positioned on a first side of a surface of the wafer and configured to direct at least a portion of a light beam through the wafer, wherein the light beam is at least partially transmittable through the wafer; a sensor positioned on a second side of the wafer opposite the first side and configured to monitor an edge bevel location of the wafer based on one or more characteristics of light transmitted through the wafer as the rotational wafer stage assembly rotates the wafer, wherein the rotational wafer stage and the light source are configured to cause the light beam to trace a pattern across the wafer proximate to the bevel of the wafer; a controller communicatively coupled to the sensor and a portion of the rotational wafer stage assembly, the controller configured to: determine a centering condition of the wafer based on the monitored one or more characteristics of light transmitted through the wafer; and responsive to the determination an off-center condition, direct the rotational stage assembly to adjust the rotational condition of the wafer.

A system for monitoring wafer slippage on a rotational wafer stage is disclosed. In one aspect, the system may include, but is not limited to, a rotational wafer stage assembly configured to secure a wafer and selectively rotate the wafer; a light source positioned on a first side of a surface of the wafer and configured to direct at least a portion of a light beam through the wafer, wherein the light beam is at least partially transmittable through the wafer; a sensor positioned on a second side of the wafer opposite the first side and configured to monitor changes in at least one of a wafer notch location and a spindle axis location as the rotational wafer stage assembly rotates the wafer; a controller communicatively coupled to the sensor and a portion of the rotational wafer stage assembly, the controller configured to: determine a slippage condition of the wafer based on the monitored changes in at least one of the wafer notch location and the spindle axis location; and responsive to the determination of a slippage condition exceeding a selected slippage threshold, direct the rotational stage assembly to adjust the rotational condition of the wafer.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention. Reference will now be made in detail to the subject matter disclosed, which is illustrated in the accompanying drawings.

Referring generally to FIGS. 1A through 3, a system for wafer crack detection is described, in accordance with the present invention. It is noted herein that the existence of cracks in semiconductor wafers may lead to significant damage to the wafers when placed in a rotating environment, such as rotation-based inspection. As such, the detection of wafer cracks prior to rotation-based inspection scanning (e.g., SURFSCAN system by KLA-TENCOR) may aid in mitigating damage to wafers as well as improving inspection throughput. The present invention, in part, is directed to a system and method for detecting cracks in semiconductor wafers. Specifically, in some embodiments, the present invention acts monitor the variability of infrared light transmitted through a spinning wafer. It is noted that analysis of this measured variability may allow a user or system to identify wafer cracks prior to or during wafer inspection scanning.

Figure 1A:
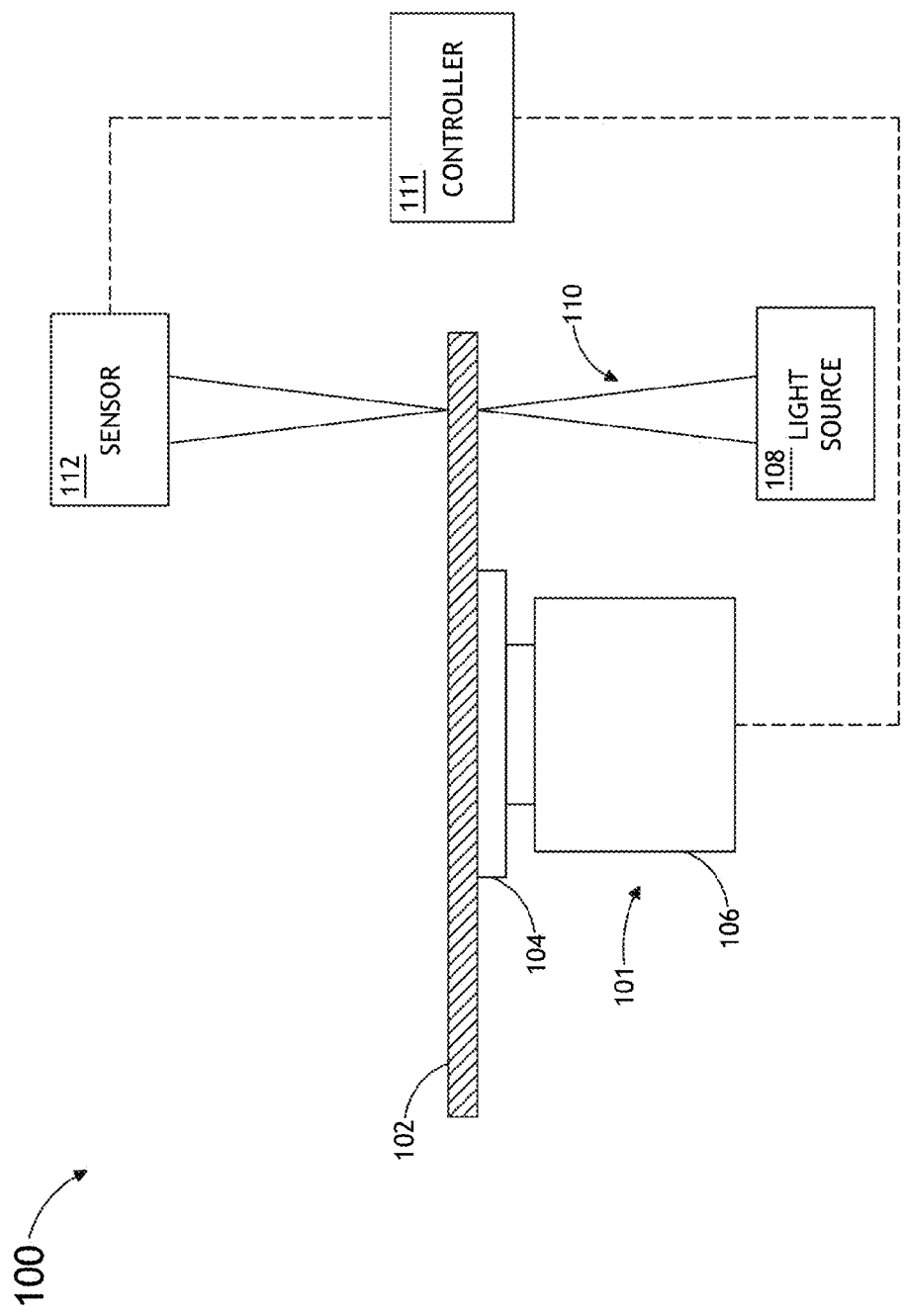
FIG. 1A is a block diagram view of a system for detecting cracks in a wafer, in accordance with one embodiment of the present invention.
Figure 1B:
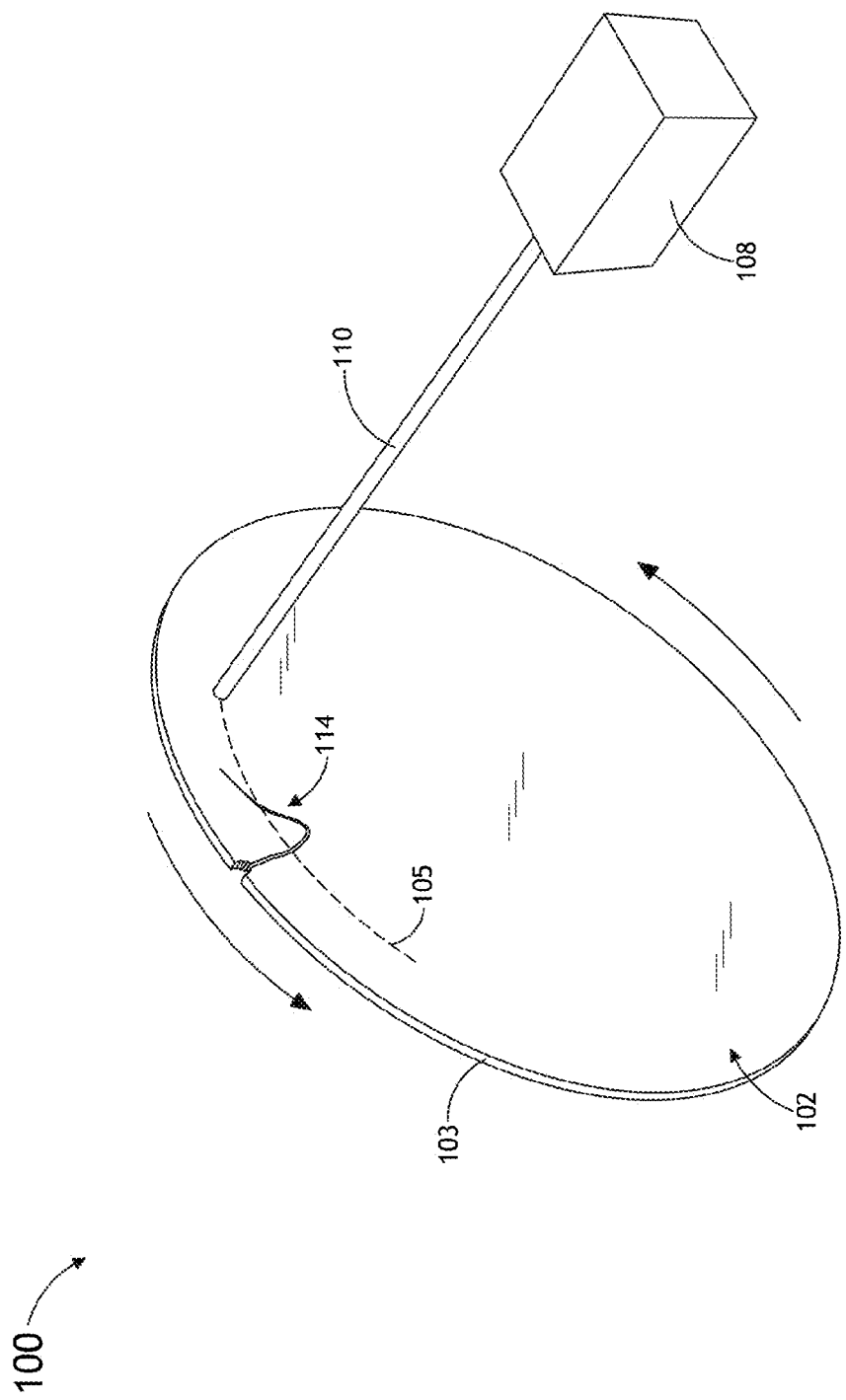
FIG. 1B is a schematic view of a system for detecting cracks in a wafer, in accordance with one embodiment of the present invention.

FIGS. 1A and 1B illustrate simplified schematic views of a system for wafer crack detection 100, in accordance with one embodiment of the present invention. In one embodiment, the wafer detection system 100 includes a rotational wafer stage assembly 101 configured to secure a wafer 102 (e.g., silicon wafer) and selectively rotate the wafer 102. In one embodiment, the rotational wafer stage assembly 101 includes a wafer chuck 104 for securing the wafer 102. It is noted herein that any wafer chuck known in the art is suitable for implementation in the present invention. For example, the wafer chuck 104 may include, but is not limited to, a vacuum chuck. In another embodiment, the rotational wafer stage assembly 101 includes a wafer spindle 106 configured to selectively rotate the wafer 102. For example, the wafer spindle 106 may rotate the wafer 102 at a selected rotational speed about an axis perpendicular to the surface of the wafer 102. As discussed further herein, the spindle 106 may selectively rotate (or stop rotation) of the wafer 102 in response to an associated controller or control system.

In another embodiment, the wafer crack detection system 100 includes a light source 108 configured to generate a light beam 110 of a selected wavelength or wavelength range. In another embodiment, the light source 108 is positioned on a first side of the wafer 102. In one embodiment, the light source 108 is configured to direct the light beam 110 onto the surface of the wafer 102. In this regard, the light source 108 may be arranged above the top surface of the wafer 102 and suitable for directing the light beam 110 toward the top surface of the wafer 102, as shown in FIG. 1A. In another embodiment, the light source 108 is suitable for generating a light beam at least partially transmittable by the wafer 102. In this regard, the wafer 102 is at least partially transparent to the radiation generated by the light source 108. It is noted herein that silicon is commonly transparent to infrared light. For example, a wafer 102 formed from silicon may be transparent to 1550 nm light. In another embodiment, the light source 108 may include any light source known in the art suitable for transmitting a light beam through a wafer or substrate. It is noted herein that bare silicon wafers are known to readily transmit light in the spectral range of approximately 1-9 μm. In one embodiment, the light source 108 may include any narrowband light source known in the art. For instance, the light source 108 may include, but is not limited to, a laser. Further, the light source 108 may include a laser capable of generating a light beam that is transmittable by the given wafer 102. In the case, for example, of a silicon wafer, the light source 108 may include, but is not limited to, an infrared laser (IR), such as a 1550 nm laser. By way of another example, the light source 108 may include a broad band source. For instance, the light source 108 may include a well collimated and filtered broadband source.

In another embodiment, the wafer crack detection system 100 includes a sensor 112 configured to monitor one or more characteristics of light transmitted through the wafer. In this regard, as the spindle 106 of the rotational stage assembly 101 rotates the wafer 102, the sensor 112 may monitor one or more characteristics of light transmitted from the light source 108 and through the wafer 102. For example, the sensor 112 may monitor the intensity of light transmitted through the wafer 102 as the wafer 102 is rotated through a given angle (e.g., partial rotation, full rotation, or multiple rotations).

For example, the sensor 112 may be positioned on a second side of the wafer 102 opposite to the first side (i.e., light source side) of the wafer. For instance, the sensor 112 may be positioned on the bottom side of the wafer 102, while the light source 108 is position on the top side of the wafer 102.

The sensor 112 of system 100 may include any light sensing detection device known in the art capable of sensing light generated by the light source 108, such as IR light, and variability in the light caused by rotating cracks of a wafer. For example, the sensor 112 may include, but is not limited to, one or more photodiodes. By way of another example, the sensor 112 may include, but is not limited to, one or more CCD detectors. By way of another example, the sensor 112 may include, but is not limited to, one or more CMOS detectors.

It is further recognized herein that the system 100 may include any number of additional optical elements to carry out the described embodiments. For example, the system 100 may further include focusing lenses to focus light from the light source 108 and one or more collimators to collimate light along the pathway between the light source 108 and sensor 112. In one embodiment, the wafer 102 is positioned at least proximate to the focus of the light beam 110. In this regard, one or more focusing lenses may be utilized to focus light emanating from the light source 108 at a position at or near the wafer plane of the wafer 102.

As shown in FIG. 1B, the light beam 110 may trace a pattern 105 across the surface of the wafer 102. In one embodiment, the light source 108 and the rotational wafer stage assembly 101 are configured to cause the light beam 110 to trace a selected pattern across the surface of the wafer 102. In this regard, the position and motion of the light source 108 relative to the wafer 102, which is actuated by the underlying rotational wafer stage assembly 101, may act to define the traced pattern 105. In another embodiment, as shown in FIG. 1B, the pattern 105 of the light beam 110 may be traced proximate to the wafer edge 103, as discussed in greater detail further herein.

It is noted herein that a crack 114 or other aberration in the wafer 102 may cause a reduction in the transmitted light intensity detected by the sensor 112 as the light beam is swept across the surface of the wafer 102. As such, the sensor 112 may serve to detect cracks in the wafer 102 by monitoring transmission intensity of the light 110 from the light source 108. For example, a drop in intensity of the transmitted light may indicate the presence of a crack (see FIG. 1C). It is noted herein that not every reduction in intensity as measured by the sensor 112 necessarily corresponds to a wafer crack. As such, a procedure is required to eliminate the frequency of false positives detected by system 100.

Referring again to FIG. 1A, the wafer crack detection system 100 includes a controller 111, in accordance with one embodiment of the present invention. In one embodiment, the controller 111 is communicatively coupled to the sensor 112 and one or more portions of the rotational wafer stage assembly 101. For example, the controller 111 may be communicatively coupled to sensor 112 and the spindle 106 of the rotational wafer stage assembly 101. It is noted herein that the controller 111 may be placed in communication with the sensor 112 and/or a portion of the rotational wafer stage assembly 101 in any manner known in the art. For example, the controller 111 may be placed in communication with the sensor 112 and/or a partition of the rotational wafer stage assembly 101 via a wireline data coupling (e.g., copper wire, optical fiber, network coupling and the like) or a wireless data coupling (e.g., RF signal).

In one embodiment, the controller 111 is configured to receive the one or more monitored light characteristics from the sensor 112. For example, the controller 111 may receive one or more signals indicative of the measured transmitted light signal from the sensor 112. In this regard, the sensor 112 may transmit the measured transmitted light intensity as a function of time or any other parameter (e.g., rotational position or spatial position on wafer).

In one embodiment, the controller 111 includes one or more processors (not shown) and a non-transitory storage medium (i.e., memory medium). In this regard, the storage medium of the controller 111 (or any other storage medium) contains program instructions configured to cause the one or more processors of controller 111 to carry out any of the various steps described through the present disclosure.

For the purposes of the present disclosure the term "processor" may be broadly defined to encompass any processor or logic element(s) having processing capabilities, which execute instructions from a memory medium. In this sense, the one or more processors of controller 111 may include any microprocessor-type device configured to execute software algorithms and/or instructions. In one embodiment, the one or more processors may consist of a desktop computer or other computer system (e.g., networked computer) configured to execute a program configured to execute the computational/data processing steps described throughout the present disclosure. It should be recognized that the steps described throughout the present disclosure may be carried out by a single computer system, multiple computer systems, or a multi-core processor. Moreover, different subsystems of the system 100, such as a display device or a user interface device (not shown), may include a processor or logic elements suitable for carrying out at least a portion of the steps described above. Therefore, the above description should not be interpreted as a limitation on the present invention but rather merely an illustration.

In one embodiment, the one or more processors of controller 111 are configured to determine the presence of one or more cracks in the wafer based on the monitored one or more characteristics of light transmitted through the wafer. It is noted herein that the controller 111 may be programmed in order to reduce the number of false positives detected by the system 100. For example, in some instances, scratches on the wafer surface may lead to a false detection event. As such, the controller 111 may be programmed to differentiate between wafer cracks and other wafer aberration, such as wafer scratches.

In another embodiment, the one or more processors of controller 111 are configured to compare the monitored one or more characteristics of the light beam 110 to a selected threshold level. For example, the selected threshold level may be selected by a user based on trial and error efforts. By way of another example, the selected threshold level may be selected by the controller 111 based on a statistical aggregation of known responses over a selected time period or operation settings. Further, the selected threshold may be applied to any of the monitored characteristics of the light transmitted through the wafer 102. For instance, the threshold may include a light intensity threshold, a duration of a change time threshold and the like, time integrated drop in intensity threshold and the like.

Figure 1C:
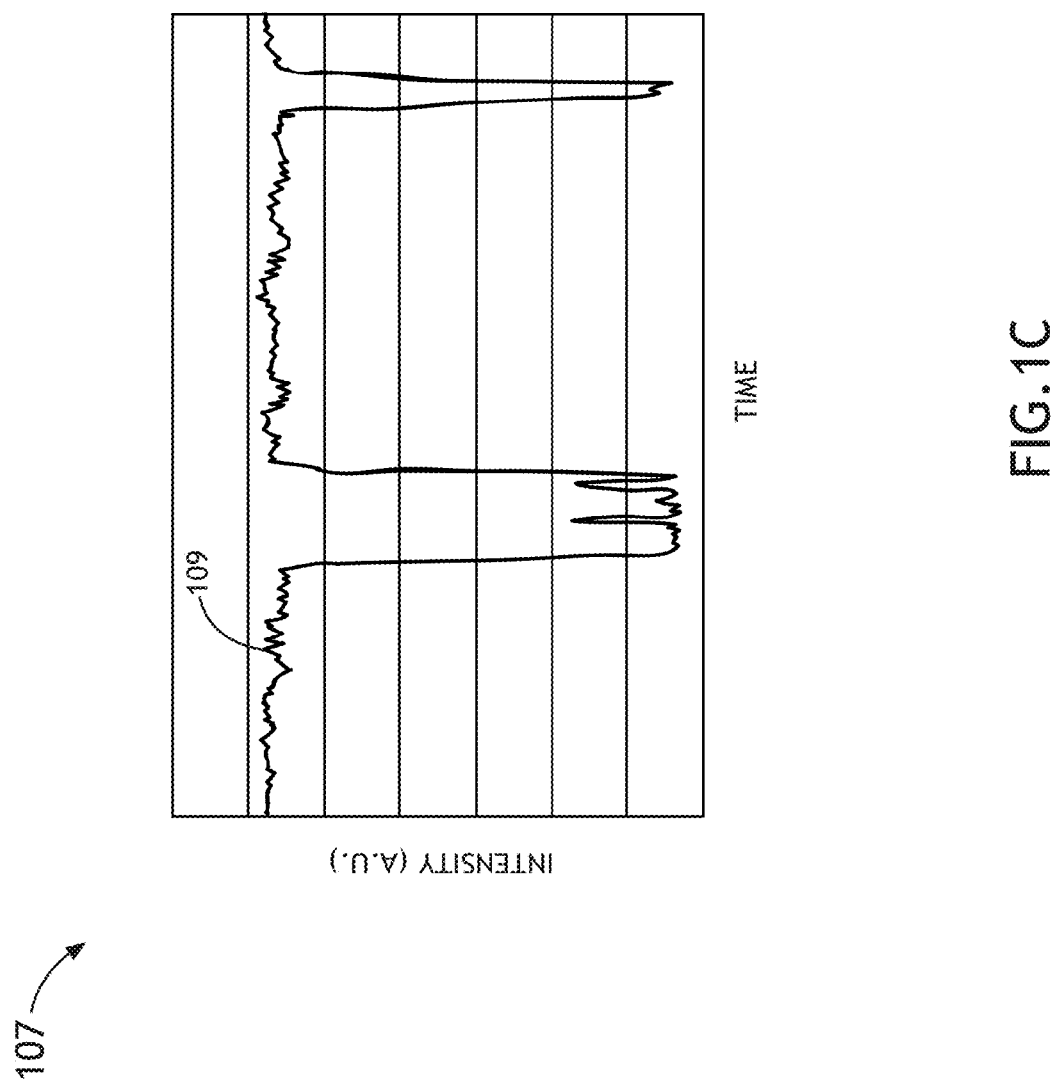
FIG. 1C is a data graph illustrating a reduction in infrared light transmitted through a wafer as a result of the presence of a wafer crack, in accordance with one embodiment of the present invention.

FIG. 1C depicts a graph 107 representative of a transmitted light signal intensity 109 monitored by the sensor 111 as a function of time, in accordance with one embodiment of the present invention. It is noted herein that the sensor 111 may detect a reduction in the transmitted light intensity over a given time span. For example, the crack 114 depicted in FIG. 1B may manifest itself in the transmitted light intensity data 109 as two drops in intensity, which correspond to the two portions of crack 114 traversed by the light beam 110 as the wafer 102 is rotated.

In another embodiment, in response to the determination of the presence of one or more cracks in the wafer 102, the one or more processors of controller 111 are configured to direct the rotational stage assembly 101 to adjust the rotational condition of the wafer 102. As previously noted herein, the system 100 may act to mitigate damage caused by the rotation of a cracked wafer by adjusting some rotational condition of the wafer 102.

In one embodiment, the adjustment of the rotational condition may include stopping the rotation of the wafer 102. For example, upon determination of a presence of one or more cracks in the wafer 102, the one or more processors of controller 111 may direct the spindle 106 of the rotational wafer stage assembly 101 to execute a braking process until a full stop of the wafer rotation is achieved.

In another embodiment, the adjustment of the rotational condition may include a reduction in speed of the rotation of the wafer 102. For example, upon determination of a presence of one or more cracks in the wafer 102, the one or more processors of controller 111 may direct the spindle 106 of the rotational wafer stage assembly 101 to execute a braking process until the rotational speed of the wafer 102 is reduced to a desired level.

It is further recognized that in some instances the controller 111 may direct the rotation wafer stage assembly 101 to increase the rotational speed of the wafer 102. In one embodiment, a wafer crack detection process, as described throughout the present disclosure, may be executed prior to an inspection process. In this regard, the wafer may undergo a wafer crack detection procedure at relatively slow rotational speeds in order to reduce the likelihood of wafer damage resulting from the rotation of a cracked wafer 102. Further, once the wafer 102 passes the wafer crack detection process, the one or more processors of controller 111 (or an independent controller of an associated inspection tool) may direct the spindle 106 of the stage assembly 101 to ramp the rotational speed of the wafer 102 up to a selected inspection tool requirement.

Figure 1D:
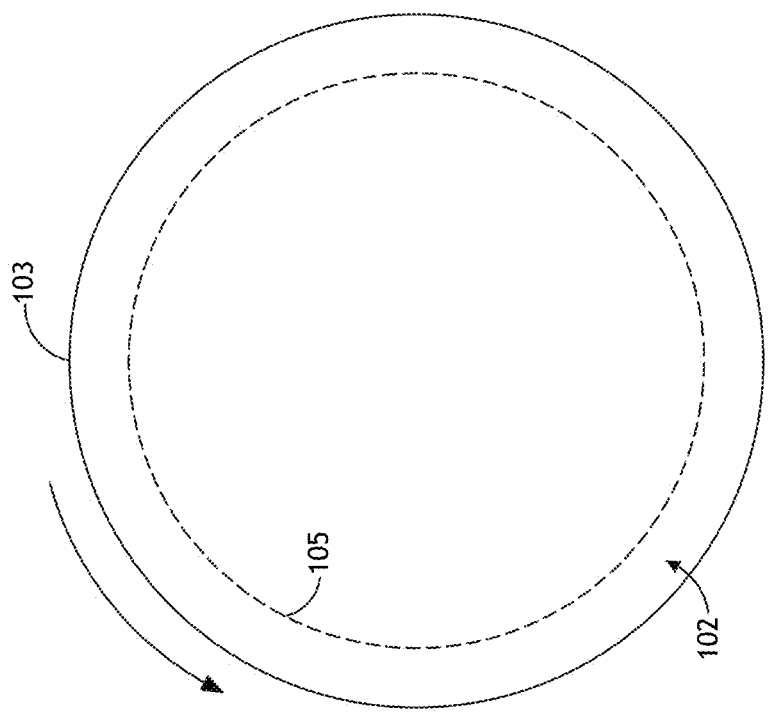
FIG. 1D is a top view of a circle pattern of a light beam traced on a rotating wafer, in accordance with one embodiment of the present invention.

FIG. 1D illustrates a top view of a one-dimensional light beam pattern 105 transmitted through wafer 102, in accordance with one embodiment of the present invention. In one embodiment, the scanning of the light beam 110 across the wafer 102 may include a one-dimensional fixed-radius scan. For example, the scanning of the light beam 110 across the wafer 102 may include a one-dimensional fixed-radius scan at any selected radius (relative to the wafer center). It is noted herein that many, if not most, wafer cracks originate from the edge 103 of a given wafer. As such, it may be particularly beneficial to monitor the edge region of a wafer 102 utilizing the system 100 of the present invention. In one embodiment, the scanning of the light beam 110 across the wafer 102 may include a one-dimensional fixed-radius scan at wafer position proximate to the edge 103 of the wafer. For example, the light source is configured to direct a light beam 110 onto the wafer 102 at a location between a laser scribe line of the wafer 102 and the bevel of the wafer 102 such that the light beam 110 substantially traces a circle pattern over the surface of the wafer 102 bounded by the laser scribe of the wafer and the bevel of the wafer 102.

Figure 1E:
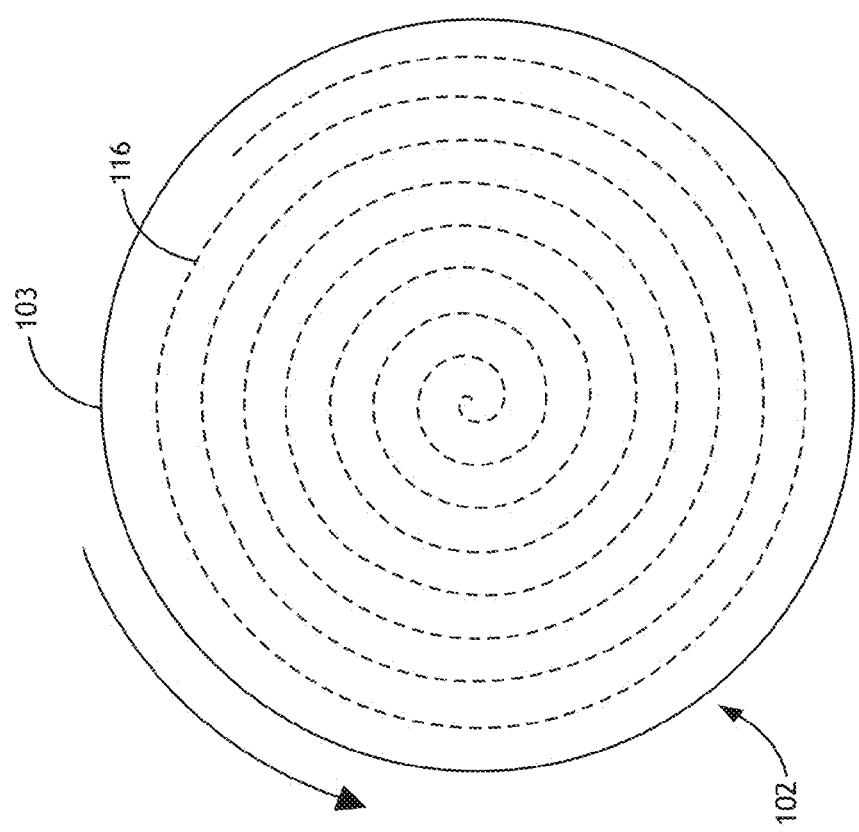
FIG. 1E is a top view of a spiral pattern of a light beam traced on a rotating wafer, in accordance with one embodiment of the present invention.

FIG. 1E illustrates a top view of a two-dimensional light beam pattern 116 transmitted through wafer 102, in accordance with one embodiment of the present invention. In one embodiment, the scanning of the light beam 110 across the wafer 102 may include a two-dimensional variable radius/variable angle scan. For example, the scanning of the light beam 110 across the wafer 102 may include a two-dimensional scanning pattern 116 that forms any scanning pattern known in the art.

For instance, as shown in FIG. 1E, the two-dimensional scanning pattern 116 may include a spiral pattern. It is noted herein that the two-dimensional scanning pattern 116 may be accomplished utilizing the rotational motion of the wafer 102 carried out by the spindle 106, the rotational wafer stage assembly 101, and an additional linear translation component. For example, the wafer stage assembly 101 may be equipped with a linear translation stage (not shown), which allows for linear translation of wafer 102 in addition to the rotational motion described throughout the present disclosure. In this regard, the linear motion of the wafer stage may translate the wafer 102 along a selected linear direction (e.g., along a radial line of wafer 102), which when coupled with the rotational motion of the wafer 102 imparted by the spindle 106, generates a spiral pattern 116, as shown in FIG. 1E.

By way of another example, the light source 108 and/or sensor 111 may be disposed on an actuatable stage. For instance, the light source 108 and/or sensor 111 may be disposed on a linear translation stage (not shown). In this regard, the linear stage may translate the light source 108 and/or sensor 111 along a selected linear direction (e.g., along a radial line of wafer 102), which when coupled with the rotational motion of the wafer 102 imparted by the spindle 106, generates a spiral pattern 116, as shown in FIG. 1E.

While the present disclosure has concentrated on an implementation setting in which the wafer 102 is transparent to the light beam 110 of light source 108, it is contemplated herein that the present invention may be extended to settings where this condition is not applicable. For example, in select wafer doping scenarios, a silicon wafer may become opaque to a light beam of the illumination. In particular, in certain doping settings, a doped silicon wafer may be substantially opaque to infrared light, such as 1550 nm light. In such settings, it is recognized herein that a forward scattering detection method may be implemented. In this regard, increased scattering caused by a crack in the wafer 102 may be detected by sensor 112. It is further noted that scattering in this case may be coupled with changes in polarization of the scattered light. As such, the present disclosure contemplates the implementation of polarizers in the light beam 110 pathway to enhance the ability to detect increases in forward scattered light caused by the presence of wafer cracks. In addition, a beam stop may be implemented on the light beam 110 in order to reduce the amount of non-forward scattered light detected by sensor 112. In this regard, the beam stop may enhance the ability of the sensor 112 to monitor light forwardly scattered by a wafer crack in wafer 102.

Figure 2:
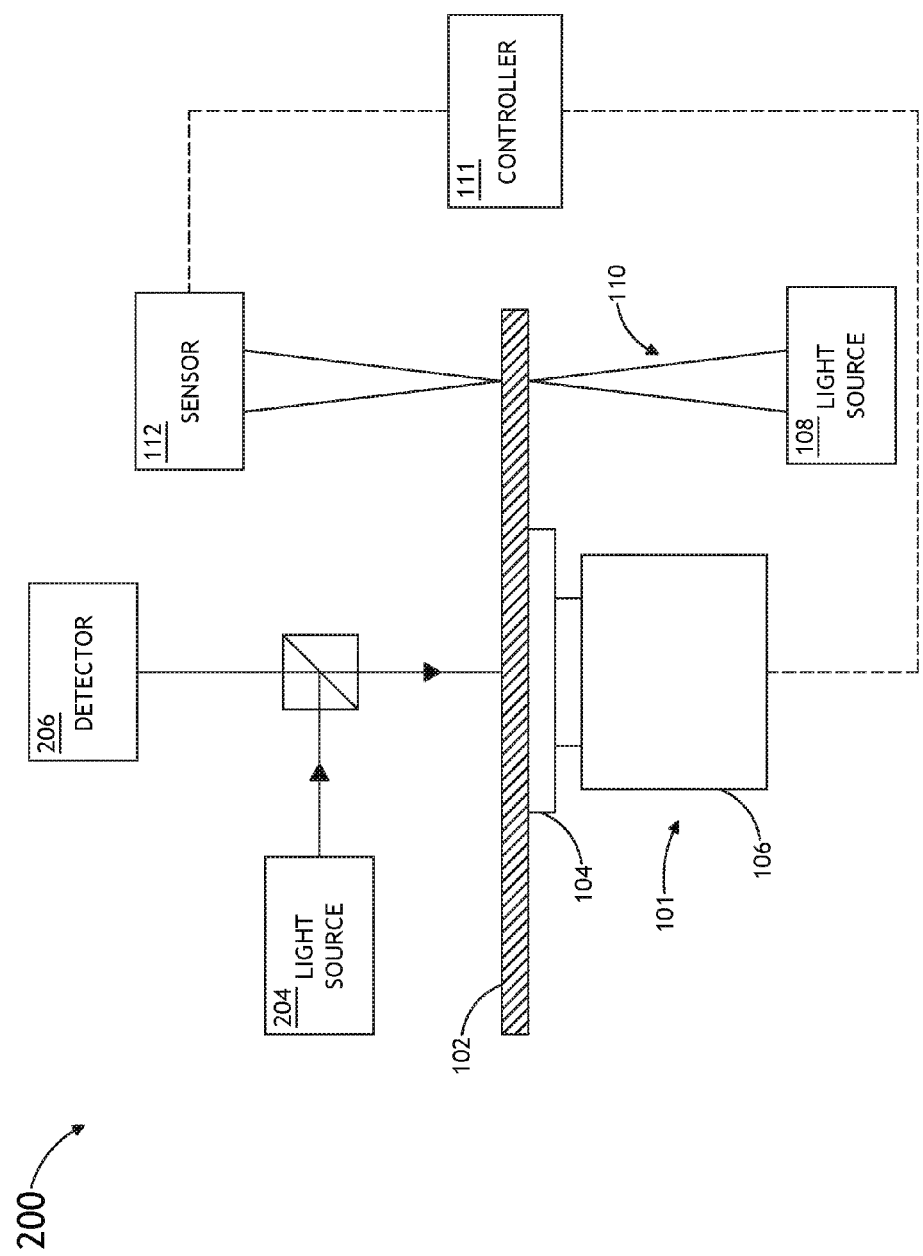
FIG. 2 is a block diagram view of an inspection tool equipped with crack detection capabilities, in accordance with one embodiment of the present invention.
Figure 3:
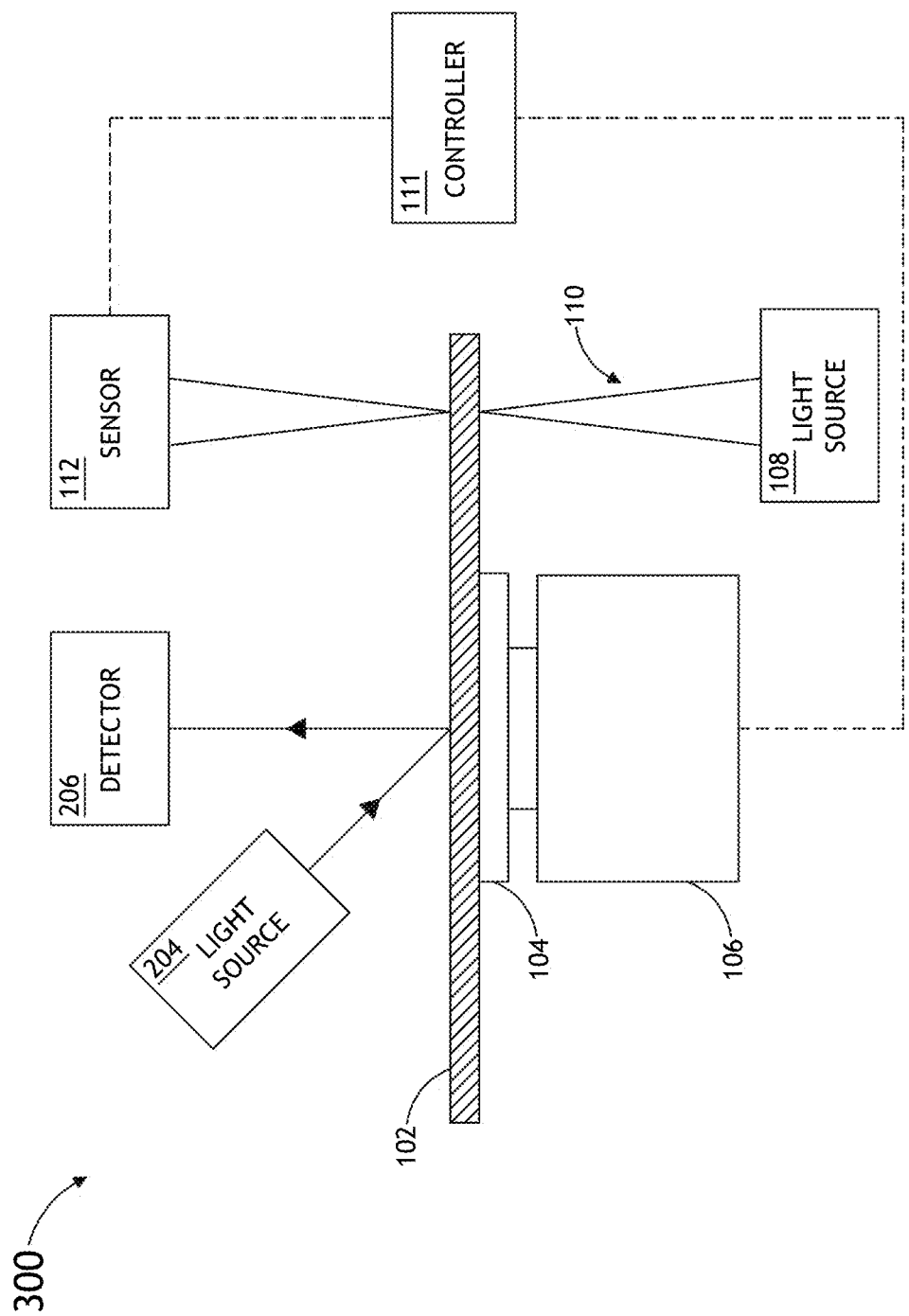
FIG. 3 is a block diagram view of an inspection tool equipped with crack detection capabilities, in accordance with one embodiment of the present invention.

FIGS. 2 and 3 illustrate simplified schematic views of a wafer inspection tool equipped with the crack detection system capabilities described previously herein, in accordance with embodiments of the present invention. In one embodiment, the wafer crack detection system 100 may be implemented within the context of any inspection tool known in the art, such as, but not limited to, the wafer inspection tools 200 and 300 described herein. In one embodiment, the wafer crack detection procedure described in the present disclosure may be implement prior to wafer inspection. In this example, a wafer 102 may be first examined by the wafer crack detection system 100. Upon passing the wafer crack detection procedure, the wafer 102 may then undergo an inspection process carried out by inspection tool 200, 300 or the like. In one embodiment, the inspection tools 200, 300 are integrated with the wafer crack detection system 100, whereby the crack detection procedure is carried out on a wafer disposed on a rotational stage of the inspection tool 200, 300.

In another embodiment, the wafer crack detection procedure may be carried out on a separate stage from the inspection scanning stage. In this context, the wafer crack detection system 100 may serve as a wafer sort step to eliminate wafers including cracks. Upon completion of the wafer detection procedure, the measured wafer may be transferred to the wafer inspection tool stage.

In another embodiment, the wafer crack detection procedure described throughout the present disclosure may be carried out during the inspection scanning process. In this regard, the light source 108 and sensor 112 may be disposed on an actuation stage or stages, allowing the light source 108 and sensor 112 to track the motion of the wafer stage of the inspection tool 200, 300. As such, the wafer detection system 100 may periodically or continually monitor a wafer 102 while it undergoes an inspection process carried out by an inspection tool 200, 300.

In a general sense, the wafer inspection tools 200 and 300 of the present disclosure may include the wafer crack detection system 100 previously described herein, at least one light source 204 (e.g., a laser) configured to illuminate an area on the surface of the wafer 102, and a detector, or camera 206, such as a CCD or TDI based detector, or a photomultiplier detector, suitable for detecting light reflected or scattered from the area illuminated by the light source. In addition, the inspection tools 200 and 300 may include a set of optical elements (e.g., illumination optics, collection optics, and the like) configured for directing (and focusing) illumination from the light source 204 onto the surface of the wafer 102 and, in turn, directing illumination from the surface of the wafer 102 to the imaging portion of the detector 206 of the inspection tools 200/300. For instance, the set of optical elements may include, but is not limited to, a primary imaging lens suitable for imaging the illuminated area on the semiconductor wafer onto a collection region of the detector. Further, the imaging detector 206 may be communicatively coupled to an image processing computer (not shown) which may identify and store imagery data acquired from the detector 206.

The inspection tools 200/300 of the present invention may be configured as any inspection system known in the art. For example, as shown in FIG. 2, the inspection tool 200 of the present invention may be configured as a bright field (BF) inspection system. Alternatively, as shown in FIG. 3, the inspection tool 300 may be configured as a dark field (DF) inspection tool. Applicant notes that the optical configurations depicted in FIGS. 2 and 3 are provided merely for illustrative purposes and should not be interpreted as limiting. In a general sense, the inspection tool 200/300 of the present invention may include any set of imaging and optical elements suitable for imaging the surface of the wafer 102. Examples of currently available wafer inspection tools are described in detail in U.S. Pat. Nos. 7,092,082, 6,702,302, 6,621,570 and 5,805,278, which are each herein incorporated by reference in the entirety.

While the present disclosure has focused on detection of wafer cracks using the light source 108 and light sensor 112 of system 100, it is further contemplated herein that the system 100 of the present disclosure may be extended to additional detection paradigms. For example, in one embodiment, the present invention may include a system and method for monitoring centering of wafer 102 on a rotational wafer stage 101. In one embodiment, the rotational wafer stage assembly 101 is configured to secure the wafer 102 and selectively rotate the wafer 102. In another embodiment, the light source 108 is positioned on a first side of a surface of the wafer and configured to direct the light beam 110 being at least partially transmittable to the wafer through the wafer 102. In another embodiment, the sensor 112 is positioned on a second side of the wafer 102 opposite the first side and configured to monitor an edge bevel location of the wafer 102 based on one or more characteristics of light transmitted through the wafer as the rotational wafer stage assembly rotates the wafer. Further, the rotational wafer stage 101 and the light source 108 are configured to cause the light beam 110 to trace a pattern 105 across the wafer proximate to the bevel of the wafer 102. In another embodiment, a controller is communicatively coupled to the sensor 112 and a portion of the rotational wafer stage assembly 101. In a further embodiment, the controller is configured to: (i) determine a centering condition of the wafer based on the monitored one or more characteristics of light transmitted through the wafer; and (ii) in response to the determination an off-center condition, direct the rotational stage assembly to adjust the rotational condition of the wafer.

It is noted herein that the various examples and embodiment related to the architecture and data processing steps of the wafer crack detection system 100 should be interpreted to extend to the above wafer slippage monitoring embodiment.

In another example, in one embodiment, the present invention may include a system and method for monitoring wafer slippage on a rotational wafer stage. In one embodiment, a rotational wafer stage assembly 101 is configured to secure a wafer 102 and selectively rotate the wafer 102. In another embodiment, the light source 108 is positioned on a first side of a surface of the wafer and configured to direct at least a portion of a light beam through the wafer 102, wherein the light beam is at least partially transmittable through the wafer. In another embodiment, the sensor 112 is positioned on a second side of the wafer 102 opposite the first side and configured to monitor changes in at least one of a wafer notch location and a spindle axis location as the rotational wafer stage assembly 101 rotates the wafer 102. In another embodiment, a controller is communicatively coupled to the sensor and a portion of the rotational wafer stage assembly. In another embodiment, the controller is configured to: (i) determine a slippage condition of the wafer based on the monitored changes in at least one of the wafer notch location and the spindle axis location; and (ii) in response to the determination of a slippage condition exceeding a selected slippage threshold, direct the rotational stage assembly to adjust the rotational condition of the wafer.

It is noted herein that the various examples and embodiment related to the architecture and data processing steps of the wafer crack detection system 100 should be interpreted to extend to the above wafer slippage monitoring embodiment.

Figure 4:
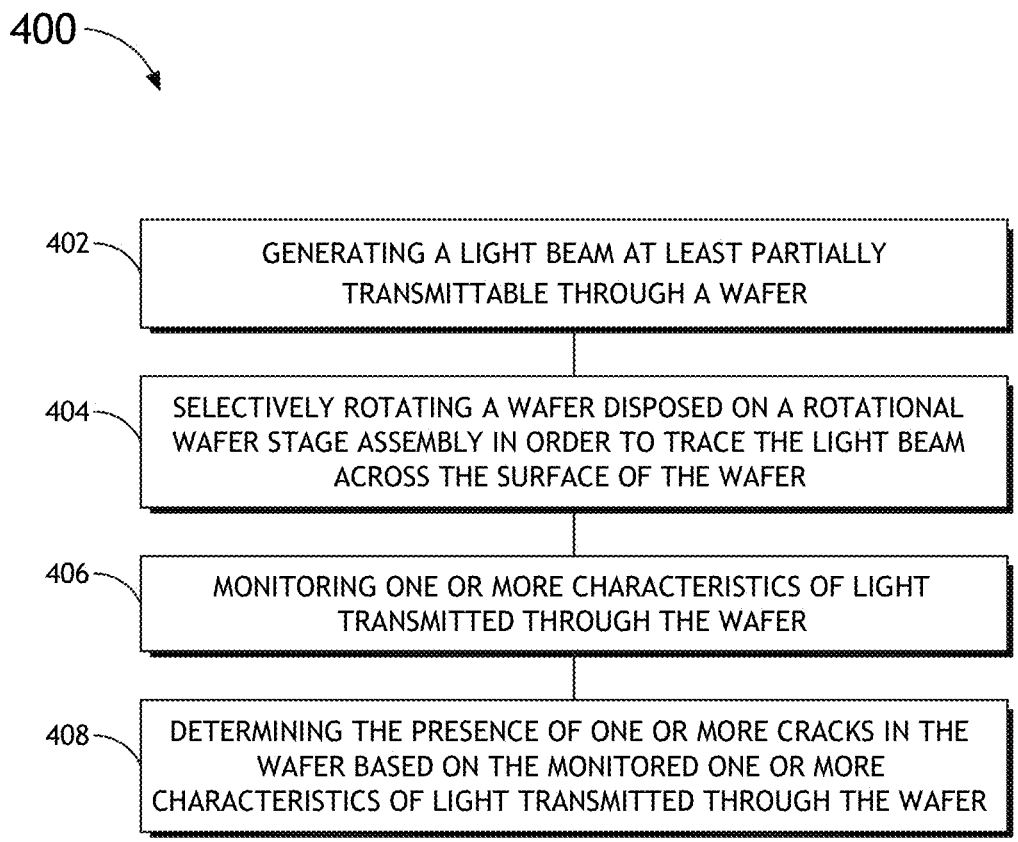
FIG. 4 is a flow diagram illustrating a method for detecting cracks in a wafer, in accordance with one embodiment of the present invention.

FIG. 4 illustrates a process flow diagram depicting a method for detecting cracks in a wafer, in accordance with one embodiment of the present invention. It is noted herein that the method 400 may be carried out utilizing any of the architectural embodiments described throughout the present disclosure. It is further noted, however, that the method 400 is not limited to the embodiments of system 100 described previously herein and may be executed by various similar or analogous systems. In a first step 402, a light beam that is at least partially transmittable through a wafer 102 is generated. For example, an infrared laser may generate a light beam having a wavelength of 1550 nm, which is generally transmittable through a bare silicon wafer. In a second step 404, a wafer 102 disposed on a rotational wafer stage assembly 101 is selectively rotated by the assembly 101 in order to trace the light beam 110 across the surface of the wafer 102. For example, the relative motion between the light source 108 and the wafer 102 may cause the light beam 110 to trace a selected pattern 105 (e.g., variable angle/fixed radius or variable angle/variable radius) across the wafer 102. In a third step 406, one or more characteristics of light transmitted through the wafer 102 are monitored using sensor 112. For example, the sensor 111 may monitor the intensity of light transmitted through the wafer 102 as the beam 110 is swept across the wafer 102. In a fourth step 408, the presence of one or more cracks in the wafer is determined by controller 111 based on the monitored one or more characteristics of light transmitted through the wafer. In a fifth step, in response to the determination of the presence of one or more cracks in the wafer 102, the controller 111 directs the rotational stage assembly to adjust the rotational condition of the wafer 102. For example, in response to a detected feature exceeding a predefined threshold, the controller 111 directs the rotational stage assembly to initiate a braking procedure on the wafer 102 in order to stop the rotational motion of the wafer 102.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A system for detecting cracks in a wafer comprising:
a rotational wafer stage assembly configured to secure the wafer and selectively rotate the wafer, wherein the rotational wafer stage assembly includes a spindle;
a light source positioned on a first side of a surface of the wafer and configured to direct at least a portion of a light beam through the wafer, wherein the light beam is at least partially transmittable through the wafer;
a sensor positioned on a second side of the wafer opposite the first side and configured to monitor one or more characteristics of light transmitted through the wafer as the rotational wafer stage assembly rotates the wafer, wherein the rotational wafer stage assembly and the light source are configured to cause the light beam to trace a pattern across the wafer; and
a controller communicatively coupled to the sensor and a portion of the rotational wafer stage assembly including the spindle, wherein the controller is configured to determine the presence of one or more cracks in the wafer based on the monitored one or more characteristics of light transmitted through the wafer,
wherein the spindle adjusts the rotational condition of the wafer in response to the determination of the presence of one or more cracks by the controller.

2. The system of claim 1, wherein the rotational wafer stage assembly includes a wafer chuck configured to secure the wafer.

3. The system of claim 1, wherein the rotational wafer stage assembly is configured to rotate the wafer about an axis perpendicular to the wafer surface.

4. The system of claim 1, wherein the rotational wafer stage assembly and the light source are configured to cause the light beam to trace substantially a circle pattern over the surface of the wafer.

5. The system of claim 4, wherein the light source is configured to direct a light beam onto the wafer at a location between the laser scribe line of the wafer and the bevel of the wafer such that the light beam substantially traces the circle pattern over the surface of the wafer bounded by the laser scribe of the wafer and the bevel of the wafer.

6. The system of claim 1, wherein the rotational wafer stage assembly and the light source are configured to cause the light beam to trace substantially a spiral pattern over the wafer.

7. The system of claim 6, wherein the light source is disposed on a linear stage, wherein the combined operation of the rotational wafer stage assembly and the linear stage of the light source cause the light beam to trace substantially the spiral pattern over the wafer.

8. The system of claim 6, wherein the light source is fixed, wherein the rotational wafer stage assembly is configured cause the light beam to trace substantially the spiral pattern over the wafer.

9. The system of claim 1, wherein the one or more characteristics of the transmitted light include the intensity of transmitted light.

10. The system of claim 1, wherein the light source comprises:
an infrared laser.

11. The system of claim 1, wherein the light source emits at least 1550 nm light.

12. The system of claim 1, wherein the sensor comprises:
at least one of a photodiode, a CCD detector and a CMOS detector.

13. The system of claim 1, wherein the plane of the wafer is located at least proximate to the focus of the light beam.

14. The system of claim 1, wherein the control system is further configured to compare the monitored one or more characteristics of the light beam to a selected response threshold.

15. The system of claim 1, wherein the adjustment of the rotational condition of the wafer by the spindle in response to the determination of the presence of one or more cracks by the controller includes stopping the rotation of the wafer.

16. The system of claim 1, wherein the adjustment of the rotational condition of the wafer by the spindle in response to the determination of the presence of one or more cracks by the controller includes reducing the speed of rotation of the wafer.

17. The system of claim 1, wherein the light source and the sensor are fixed.

18. The system of claim 1, wherein at least one of the light source and the sensor are disposed on an actuatable stage.

19. An inspection tool equipped with crack detection capabilities comprising:
- a light source configured to illuminate an area of a surface of the wafer disposed on a rotational wafer stage assembly configured to secure the wafer and selectively rotate the wafer, wherein the rotational wafer stage assembly includes a spindle;
- a detector configured to detect light reflected or scattered from the illuminated area of the wafer;
- a crack detection light source positioned on a first side of a surface of the wafer and configured direct at least a portion of a light beam through the wafer, wherein the light beam is at least partially transmittable through the wafer;
- a crack detection sensor positioned on a second side of the wafer opposite the first side and configured to monitor one or more characteristics of light transmitted through the wafer as the rotational wafer stage assembly rotates the wafer, wherein the rotational wafer stage assembly and the light source are configured to cause the light beam to trace a pattern across the wafer; and
- a controller communicatively coupled to the sensor and a portion of the rotational wafer stage assembly including the spindle, wherein the controller is configured to determine the presence of one or more cracks in the wafer based on the monitored one or more characteristics of light transmitted through the wafer,
- wherein the spindle is configured to adjust the rotational condition of the wafer in response to the determination of the presence of one or more cracks by the controller.

20. The inspection tool of claim 19, wherein the inspection tool is configured as at least one of a bright-field inspection tool and a dark-field inspection tool.

21. A method for detecting cracks in a wafer comprising:
- generating a light beam at least partially transmittable through the wafer with a light source positioned on a first side of the wafer, wherein the light source is configured to direct at least a portion of a light beam through the wafer;
- selectively rotating a wafer disposed on a rotational wafer stage assembly including a spindle in order to trace the light beam across the surface of the wafer;
- monitoring one or more characteristics of light transmitted through the wafer with a sensor positioned on a second side of the wafer opposite the first side and configured to monitor one or more characteristics of light transmitted through the wafer as the rotational wafer stage assembly rotates the wafer, wherein the rotational wafer stage assembly and the light source cause the light beam to trace a pattern across the wafer;
- determining the presence of one or more cracks in the wafer based on the monitored one or more characteristics of light transmitted through the wafer; and
- adjusting the rotational condition of the wafer, with the spindle, in response to the determination of the presence of one or more cracks in the wafer.

22. A system for monitoring centering of wafer on a rotational wafer stage comprising:
- a rotational wafer stage assembly configured to secure a wafer and selectively rotate the wafer, wherein the rotational wafer stage assembly includes a spindle;
- a light source positioned on a first side of a surface of the wafer and configured direct at least a portion of a light beam through the wafer, wherein the light beam is at least partially transmittable through the wafer;
- a sensor positioned on a second side of the wafer opposite the first side, the sensor positioned so as to monitor an edge bevel location of the wafer based on one or more characteristics of light transmitted through the wafer as the rotational wafer stage assembly rotates the wafer, wherein the rotational wafer stage and the light source are configured to cause the light beam to trace a pattern across the wafer proximate to the bevel of the wafer; and
- a controller communicatively coupled to the sensor and a portion of the rotational wafer stage assembly including the spindle, wherein the controller is configured to determine a centering condition of the wafer based on the monitored one or more characteristics of light transmitted through the wafer,
- wherein the spindle is configured to adjust the rotational condition of the wafer in response to the determination of an off-center condition by the controller.

23. A system for monitoring wafer slippage on a rotational wafer stage comprising:
- a rotational wafer stage assembly configured to secure a wafer and selectively rotate the wafer, wherein the rotational wafer stage assembly includes a spindle;
- a light source positioned on a first side of a surface of the wafer and configured direct at least a portion of a light beam through the wafer, wherein the light beam is at least partially transmittable through the wafer;
- a sensor positioned on a second side of the wafer opposite the first side and configured to monitor changes in at least one of a wafer notch location and a spindle axis location as the rotational wafer stage assembly rotates the wafer; and
- a controller communicatively coupled to the sensor and a portion of the rotational wafer stage assembly including the spindle, wherein the controller is configured to determine a slippage condition of the wafer based on the monitored changes in at least one of the wafer notch location and the spindle axis location,
- wherein the spindle is configured to adjust the rotational condition of the wafer in response to the determination of a slippage condition exceeding a selected slippage threshold by the controller.

* * * * *